(12) United States Patent
Pianzola et al.

(10) Patent No.: US 8,357,334 B2
(45) Date of Patent: *Jan. 22, 2013

(54) METHODS AND DEVICES FOR THE PRODUCTION OF CYANOPYRIDINES

(75) Inventors: Daniel Pianzola, Glis (CH); Anton Zenklusen, Baltschieder (CH)

(73) Assignee: Lonza Ltd., Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/904,197

(22) Filed: Oct. 14, 2010

(65) Prior Publication Data

US 2011/0092710 A1 Apr. 21, 2011

Related U.S. Application Data

(60) Provisional application No. 61/252,354, filed on Oct. 16, 2009.

(51) Int. Cl.
*F27B 15/08* (2006.01)
*G05D 7/00* (2006.01)
*B01J 19/00* (2006.01)
*C07D 211/00* (2006.01)

(52) U.S. Cl. ......... 422/187; 422/198; 514/277; 546/286

(58) Field of Classification Search ................... 422/187, 422/198; 514/277; 546/286
See application file for complete search history.

(56) References Cited

U.S. PATENT DOCUMENTS

| 2,861,299 A | 11/1958 | Day |
| 3,929,811 A | 12/1975 | Gelbein et al. |
| 2008/0039632 A1 * | 2/2008 | Matz et al. .................... 546/286 |
| 2011/0092709 A1 * | 4/2011 | Pianzola et al. ............. 546/286 |

FOREIGN PATENT DOCUMENTS

| CN | 101045706 A1 | 10/2007 |
| EP | 0726092 A1 | 8/1996 |
| WO | 9532055 | 11/1995 |
| WO | 03022819 | 3/2003 |
| WO | 2004071657 | 8/2004 |
| WO | WO 2004/071657 A1 * | 8/2004 |
| WO | 2005016505 A2 | 2/2005 |

* cited by examiner

*Primary Examiner* — Susannah Chung
(74) *Attorney, Agent, or Firm* — Hoffmann & Baron, LLP

(57) ABSTRACT

Subject of the invention is a method for the production of a cyanopyridine, comprising the steps of
(a) providing a column comprising an absorber section and a stripping section, the absorber section being positioned above the stripping section, such that liquid which passed the absorber section enters the stripping section,
(b) feeding a gaseous phase comprising the cyanopyridine into the column,
(c) contacting the gaseous phase with an aqueous solution in the absorber section, such that at least a portion of the cyanopyridine is dissolved in the aqueous solution,
(d) stripping the aqueous solution obtained from the absorber section in step (c) with a stripping gas in the stripping section, and
(e) eluting an aqueous solution comprising the cyanopyridine from the bottom of the column.
Another subject of the invention is a device for carrying out the invention.

15 Claims, 1 Drawing Sheet

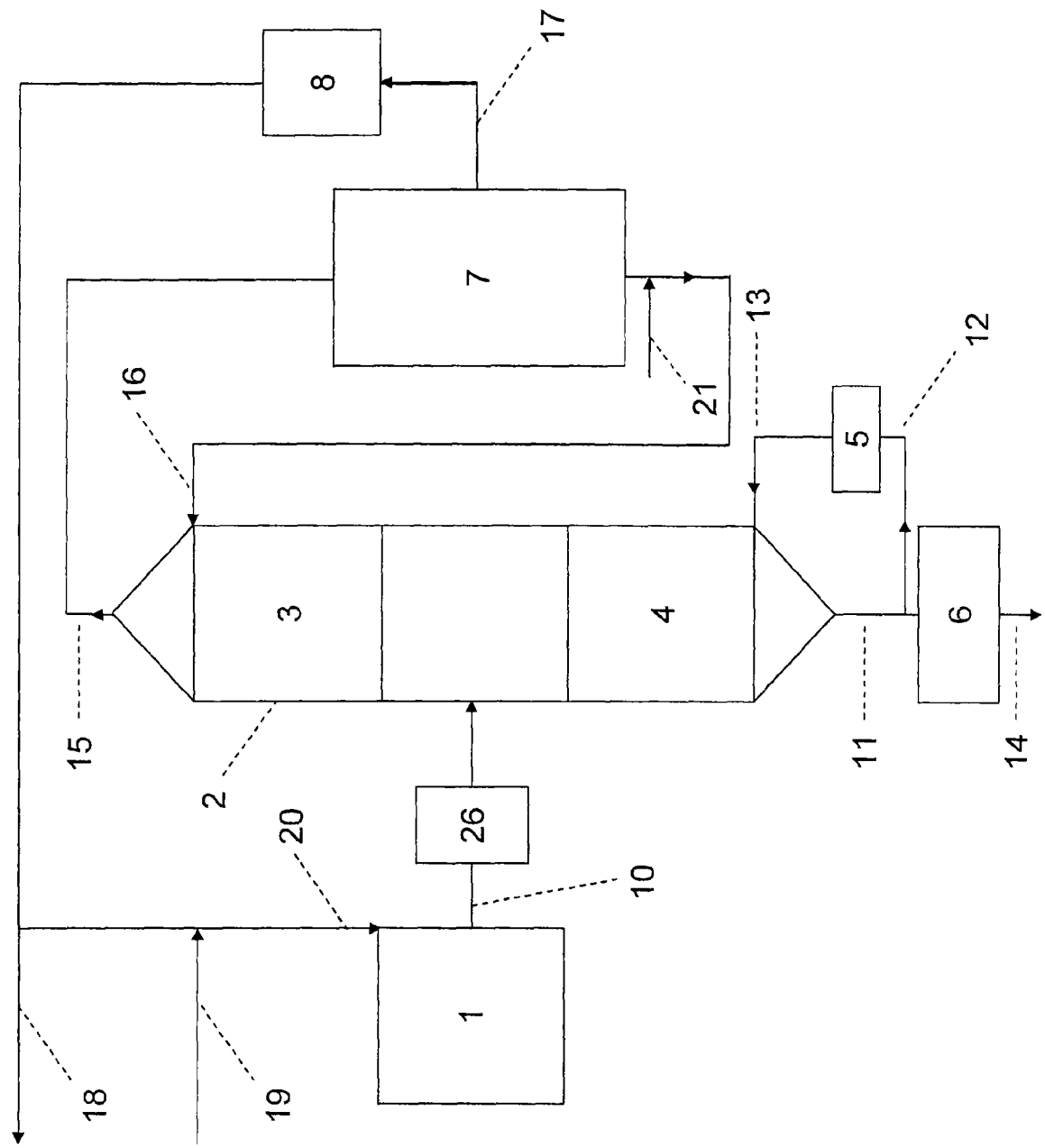

METHODS AND DEVICES FOR THE PRODUCTION OF CYANOPYRIDINES

CROSS REFERENCE TO RELATED APPLICATIONS

This application is based on, and Applicants claim priority from, U.S. Provisional Application bearing Ser. No. 61/252,354 filed Oct. 16, 2009, the disclosure of which is incorporated herein by reference.

The invention relates to methods and devices for the production of cyanopyridines from alkylpyridines.

BACKGROUND OF THE INVENTION

Cyanopyridines are important starting materials for the production of pharmaceutical intermediates and other compounds. 3-methylpyridine (3-picoline) is an intermediate in the industrial production of nicotinic amide and nicotinic acid, which are essential vitamins of the vitamin B-complex (vitamin $B_3$).

Methods for the production of cyanopyridines from methylpyridines are known in the art. Commonly, the cyanopyridines are oxidized in the presence of a catalyst with ammonia and oxygen. The process is referred to as "ammoxidation" or "oxidative ammonolysis". Various catalysts are known, which comprise specific combinations of catalytic components, which can be coated on carrier materials.

WO 03/022819 discloses methods for the production of heteroaromatic nitriles by ammoxidation of the corresponding alkyl-substituted pyridines. Methods and catalysts for oxidative ammonolysis of alkylpyridines are also disclosed in WO 95/32055.

After the ammoxidation reaction, a gaseous mixture is obtained, which comprises cyanopyridine, ammonia, residual methylpyridines, side products such as pyridine, carbon dioxide, hydrogen cyanide, water and gases of the reaction stream, such as oxygen and nitrogen. It is thus necessary to isolate the cyanopyridine from this mixture. Various methods are known in the art to separate the product from the other components.

In the art, methods for isolating the cyanopyridine are known, in which the cyanopyridine is quenched and extracted with an organic solvent.

U.S. Pat. No. 2,861,299 discloses a method for obtaining cyanopyridine from a reaction product, in which the reaction product is passed through a cooling condenser, a dry ice-catcher and a glass wool filter and extracted in a collector using an inert solvent such as benzene. The extraction with benzene as a quenching agent is also disclosed in U.S. Pat. No. 3,929,811.

However, the use of organic quenching agents is disadvantageous, because organic solvents such as benzene are relatively expensive, toxic and inflammable. Further, the use of organic solvents in an industrial quenching process is problematic, because the gaseous phase is enriched in organic solvents and explosive even at room temperature. Thus the reaction product has to be cooled to low temperatures before and during quenching. The waste gas comprises high levels of organic solvent and has to be treated. Quenching methods with organic solvents are thus complicated and require a large number of process steps.

US 2008/0039632 discloses a method for quenching a gaseous reaction product comprising cyanopyridine with a predominantly non-aqueous quenching fluid. The quenching fluid comprises picoline, which is the starting compound of the ammoxidation reaction and thus can be retransferred to the reactor. However, picoline is explosive when mixed with air, and thus the process requires specific safety measures such as reducing and controlling the temperature and the oxygen content. After cooling the picoline in the separation step, it has to be transferred to the reactor and reheated, and thus the overall process requires a large amount of energy.

In order to overcome the problems associated with quenching with organic solvents, methods have been developed in the art in which the use of an organic solvent is not necessary.

CN101045706 A discloses a method in which the gaseous product obtained from the ammoxidation reaction is brought into contact with a circulatory aqueous solution in two absorption towers, in order to obtain an aqueous solution of 3-cyanopyridine. Since cyanopyridine is hydrolyzed to nicotinic acid at elevated temperatures and at a high concentration, it is necessary to control the concentration of 3-cyanopyridine in the absorption towers and in the product below 10 wt. %. Further, it is necessary to control the temperature of the circulatory aqueous solution, and thus the temperature in the two absorbent towers, to below 50° C., preferably between 15 and 30° C. When choosing such a low concentration and temperature, more than 95% of the product is recovered.

However, the concentration of the product in the final solution is relatively low and it would be desirable to obtain the product at a higher concentration. Further, the loss of 5% cyanopyridine by hydrolysis is still relatively high. The gaseous product, from which the cyanopyridine was separated, is not reused in the process. Residual picoline is lost and the process requires at least two absorption towers.

PROBLEM UNDERLYING THE INVENTION

The problem underlying the invention is to provide a method for the preparation of cyanopyridines, which overcomes the above-mentioned disadvantages.

Specifically, the problem underlying the invention is to provide an improved method for the preparation of cyanopyridines, in which the cyanopyridines are separated from a gaseous mixture without the use of an organic solvent to absorb the cyanopyridine. The cyanopyridine shall be obtained at a high yield. The hydrolysis of the cyanopyridine during the process shall be kept at a low level.

Another problem underlying the invention is to provide a process for the preparation of cyanopyridines, in which the cyanopyridine is obtained at high purity. Specifically, the cyanopyridine shall be obtained in an aqueous solution at a high concentration.

Another problem underlying the invention is to provide a method for the preparation of cyanopyridines, which can be carried out as a closed and circular process. Specifically, the aqueous solution shall be maintained in the process. The gaseous mixture, which remains after separation of the cyanopyridines, shall be maintained in the process at least in part.

Another problem underlying the invention is to provide a relatively simple device for the preparation of cyanopyridines from gaseous mixtures. The device shall comprise a low number of components. It shall be usable in a simple manner and continuously over a long time period.

Altogether, the process and the device shall enable the purification of cyanopyridines with a low level of waste products and thus in an environmentally acceptable manner.

DISCLOSURE OF THE INVENTION

Surprisingly, the problem underlying the invention is solved by the methods and devices according to the claims. Further inventive embodiments are disclosed throughout the description.

Subject of the invention is a method for the production of a cyanopyridine, comprising the steps of
(a) providing a column comprising an absorber section and a stripping section, the absorber section being positioned above the stripping section, such that liquid which passed the absorber section enters the stripping section,
(b) feeding a gaseous phase comprising the cyanopyridine into the column,
(c) contacting the gaseous phase with an aqueous solution in the absorber section, such that at least a portion of the cyanopyridine is dissolved in the aqueous solution,
(d) stripping the aqueous solution obtained from the absorber section in step (c) with a stripping gas in the stripping section, and
(e) eluting an aqueous solution comprising the cyanopyridine from the bottom of the column.

The column is preferably an industrial column. Absorber columns and stripping columns are common components of industrial chemical process devices and known in the art. In the method of the present invention, a column is used which comprises an absorber section and a stripping section. However, the inventive process may also be carried out in a laboratory scale.

In the inventive process, an aqueous solution is introduced on top of the column or near the top of the column, passes the absorber section and the stripping section and is eluted at the bottom or near the bottom of the column. When passing the column from top to bottom, the aqueous solution has taken up cyanopyridine.

The stripping gas which is introduced at the bottom of the column or near the bottom of the column passes the stripping section and the absorber section and is let out at the top of the column or near the top of the column. In summary, a gas stream and a liquid stream can move in the column in opposite directions towards each other.

According to the invention, any device is defined as a column, in which an absorber section is combined with a stripping section as outlined above. In one embodiment, the column is a single tower, which has a uniform outer metal wall. In another embodiment, the absorber section and the stripping section are within distinct columns, i.e. an absorber column and a stripping column, both columns being connected, the absorber column being arranged on top of the stripping column, such that both columns together form column. Thus the design and geometry of the column is at the skilled person's discretion, as long as the necessary gas and liquid flow and control of the cyanopyridine absorption and stripping are enabled.

The absorber section is a typical liquid/gas absorber section as known in the art. At the top or above the absorber section, there is an inlet for adding water, preferably pure water. The absorber section comprises devices for letting the aqueous solution flow or drip downwards slowly. Designs and devices are known in the art, which enable good contact between the up flowing gas and the down flowing liquid in the absorber section. Preferably, the absorber section comprises trays or plates, which are known as bubble-cap trays or plates in the art. The column may comprise 2 to 40 or 5 to 20 trays or plates. In general, the more trays are provided, the more cyanopyridine is dissolved. The contact between the gas and the liquid in the absorber section can also be enhanced by other means, for instance packing materials. The packing materials can either be a poured or an ordered package. Ordered packages are preferred, because they are highly efficient especially when the ratio of liquid/gas is low.

In a preferred embodiment of the invention, the temperature of the liquid in the absorber section is between 40 to 90° C., preferably between 50 and 80° C. The temperature can be achieved without active cooling within the column, when it is the saturation temperature of the gas stream.

In a preferred embodiment of the invention, the gaseous phase is fed into the column in step (b) at a position of the column, which is below the absorber section and above the stripping section. Thus, the gaseous phase can stream upwards into the absorber section to an outlet at or near the top of the column. The gaseous phase does not or not significantly enter the stripping section.

In the stripping section, components are removed from the aqueous solution by a vapour stream. Columns and devices for stripping liquids are known in the art. In a preferred embodiment, the stripping section is a packed or trayed column. The aqueous solution comprising at least a portion of the cyanopyridine, which has passed the absorber section, enters the stripping section. When passing the stripping section and dripping or streaming downwards, the liquid is contacted with a stripping gas. The stripping gas is introduced at the bottom, or near the bottom of the column and below or near the bottom of the stripping section. The stripping section comprises means for enhancing the contact of the liquid phase with the vapour phase. In a preferred embodiment, the stripping section is a trayed tower. In the trays, the liquid flows back and forth horizontally, while the vapour bubbles up through holes and the trays. Thereby, the contact area between the liquid and the vapour phase is enhanced. In another embodiment, or in addition, the stripping section can be a packed column, preferably an ordered package. The stripping section used according to the invention is not limited to these specific embodiments, and any design known in the art is applicable, in which an aqueous solution is stripped from volatile components.

In the stripping section, components from the aqueous cyanopyridine solution, which are more volatile than water, are removed. These are components having a higher partial pressure in aqueous solution compared to their partial pressure in the gas phase. Specifically, ammonia is removed in the stripping section. This is advantageous, because ammonia induces the hydrolysis of cyanopyridine. Further, gaseous components, such as $N_2$, carbon dioxide, hydrogen cyanide, oxygen and aromatic components, such as pyridine and methylpyridines, are removed.

In a preferred embodiment of the invention, the stripping gas is water steam. The stripping of the aqueous solution with water steam is advantageous, because no further gaseous component is introduced into the process and dissolved in the aqueous solution. The water steam can be condensed and become part of the aqueous solution. The water steam can be generated by known means. In a preferred embodiment of the invention, the water steam is obtained from a boiler.

In a preferred embodiment of the invention, the temperature in the stripping section is between 90 and 115° C., preferably between 100 and 110° C. depending on the pressure. Components which have a higher partial pressure in the liquid phase compared to their partial pressure in the gas phase are stripped from the aqueous solution. In a preferred embodiment, the pressure in the column is maintained as equal to or slightly above or slightly lower than air pressure. For instance, the pressure may be between 500 and 2000, or between 700 and 1700, or between 1000 and 1300 mbar.

The aqueous solution is collected at the bottom of the column. The aqueous solution comprises the cyanopyridine. In a preferred embodiment of the invention, the aqueous solution is cooled to a temperature below 50° C., preferably below 40° C. during and/or after the elution (e) by a cooler. The cooling of the aqueous solution inhibits the hydrolysis of cyanopyridine.

Since cyanopyridines can be subjected to hydrolysis at high temperatures, the overall time for which the cyanopyridines are kept in column at elevated temperature shall be reduced to a minimum. When the aqueous solution enters the bottom of the column after passing the stripping section, the solution should be eluted from the column as soon as possible. When using the column with the absorber and stripping section as outlined above, it is possible to extract the cyanopyridine from the gaseous reaction product within a relatively short time. For instance, the average time span between feeding the reaction product into the column and eluting the cyanopyridine can be adjusted to less than 1 hour. Although elevated temperatures are applied in the column, the loss of cyanopyridine due to hydrolysis is low, for instance about less than 2 wt %. Preferably, the overall yield of cyanopyridine is above 98%, based on the total cyanopyridine fed into column.

In a preferred embodiment of the invention, the aqueous solution eluted in step (e) comprises more than 15 wt. % cyanopyridine, or preferably more than 25 or more than 30 wt. %. The aqueous solution eluted in step (e) may comprise 15 to 45 or 25 to 40 wt. % cyanopyridine. Subsequently, the cyanopyridine can be separated from the water by known methods. In a preferred embodiment, the cyanopyridine is extracted with an organic solvent, for example with toluene.

In a preferred embodiment of the invention, the gaseous phase comprising the cyanopyridine is produced in a reactor, in which an oxidative ammonolysis of an alkylpyridine is carried out. This reaction comprises a step of contacting the alkylpyridines with a catalyst in the presence of ammonia and oxygen. The method is thus an oxidative ammonolysis (ammoxidation). Usually, oxygen is supplied to the process by air. The gaseous product obtained from an ammoxidation reaction comprises nitrogen (as the main component), carbon dioxide, water vapour, ammonia, oxygen and the product cyanopyridine. Further, unreacted alkylpyridine and pyridine and derivatives thereof as side products are present. Methods for producing cyanopyridines from alkylpyridines by oxidative ammonolysis in the presence of catalysts are known in the art. Such processes are disclosed for instance in WO 03/022819, WO 2005/016505, WO 2004/071657 or EP 0726092 A1. The processes for the production of cyanopyridines from alkylpyridines disclosed therein are incorporated by reference.

After the ammoxidation reaction, the gaseous phase has a high temperature, usually about 300 to about 450° C. The gaseous phase from the reactor can be fed into the column directly or can be precooled prior to feeding it into the column in step (b). For instance, the gaseous phase can be cooled to a temperature between approximately 150 and 200° C. The energy gained during precooling can be reused in the overall process.

In a preferred embodiment of the invention, in the reactor the alkylpyridine is contacted with a catalyst in the gaseous phase. In a preferred embodiment of the invention, the alkylpyridine is 3-methylpyridine and thus the cyanopyridine is 3-cyanopyridine. In further embodiments of the invention, the alkylpyridine is 1-methylpyridine and the cyanopyridine is 1-cyanopyridine, or the alkylpyridine is 2-methylpyridine and the cyanopyridine is 2-cyanopyridine. It is also possible to use a mixture of alkylpyridines as starting components. Further, alkylpyridines having two or more alkyl moieties may be used, such as lutidine.

In a preferred embodiment of the invention, the gaseous phase, which passed the absorber section, is let out at the top of the column and transferred to a condenser, in which an aqueous condensate is obtained. Further, organic components with a low vapour point are collected. Preferably, residual cyanopyridine is condensed at this step, if present. The temperature of the condenser is preferably kept at 20-50° C., more preferably 30-40° C.

In specific embodiments, the condenser is a heat exchanger cooled by a cooling medium, or it is a column, in which the condensate is kept in circulation over the column. The condensate is cooled during circulation.

In a preferred embodiment of the invention, the aqueous condensate is refed into the absorber section of the column. When refeeding the aqueous condensate into the column, the overall process can be carried out without discarding aqueous solution.

In a preferred embodiment of the invention, at least a portion of the gaseous phase, which passed the condenser, is introduced into the reactor. When refeeding the gaseous phase into the reactor, the overall amount of waste gas can be reduced significantly. However, since during the reaction the reaction gas is depleted of oxygen, a portion of the gaseous phase should be replaced by fresh air, thereby adapting the oxygen level to the necessary level. It was found that this can be achieved by replacing approximately 20% of the gaseous phase by fresh air. In preferred embodiments, approximately 5% to 40 vol. % or 10% to 30 vol. % of the gaseous phase from the condenser is replaced by air, before refeeding it into the reactor.

In a preferred embodiment of the invention, the pressure in the process is adjusted by a compressor or a ventilator.

In a preferred embodiment of the invention, the process is a closed process, in which the aqueous phase, which is not eluted from the column in step (e), is refluxed, and/or in which at least a portion of the gaseous phase, preferably more than 50 vol. %, is refluxed. According to the invention, a "closed process" means that essentially no gas or liquid is withdrawn or added unless at the positions indicated. In the closed process, water which is eluted in step (e) is replaced. It is preferred that the water is added at the top of the column into the absorber section, but the water could also be added at other positions. Specifically, no waste liquid or only a low amount of waste liquid is discarded. Preferably, the aqueous solution circulates and an aqueous product is obtained at the bottom of the column. The gas pressure may be controlled by valves.

The method of the invention is a method for the production of a cyanopyridine. This means that at least one cyanopyridine is produced. The method is also a method for the production of an aqueous solution of a cyanopyridine, a method for isolation of a cyanopyridine and a method for purification of a cyanopyridine.

Another subject of the invention is a device for the production of a an aqueous solution of a cyanopyridine, comprising
a column comprising an absorber section and a stripping section,
the absorber section being positioned above the stripping section, such that liquid which passed the absorber section enters the stripping section,
means for feeding a gaseous phase comprising the cyanopyridine into the column,
the absorber section being adapted for contacting the gaseous phase with an aqueous solution, such that at least a portion of the cyanopyridine is dissolved in the aqueous solution,
the stripping section being adapted for stripping the aqueous solution from the absorber section with a stripping gas, and
means at the bottom of the column for eluting the aqueous solution.

The device of the invention is applicable and adapted for carrying out the method of the invention. Thus the specific embodiments outlined above relating to the method of the invention are applicable in the device of the invention. Another subject of the invention is the use of the device of the invention in a method of the invention.

In a preferred embodiment of the invention, the column further comprises means at the top of the column for transferring the gaseous phase, which passed the absorber section, to a condenser, in which an aqueous condensate is obtained.

In a preferred embodiment of the invention, the condenser comprises means for feeding the aqueous condensate from the condenser into the absorber section of the column and/or means for transferring the gaseous phase, which passed the condenser, into the reactor.

In a preferred embodiment of the invention, the device further comprises a boiler for providing water steam to the stripping section and/or a cooler for cooling the aqueous solution after the elution (e). In a preferred embodiment of the invention, the device further comprises a cyanopyridine. When the device is in use, it comprises a gaseous reaction product in column comprising cyanopyridine and an aqueous solution in column comprising cyanopyridine.

The device comprises means for transporting gases and liquids, such as pipes, with respective inlets and outlets. The pipes, inlets and outlets may comprise controlling means for adjusting and controlling the flow, such as valves and pumps. The gas flow can be adjusted by compressors and ventilators.

The method and the device of the invention solve the above-mentioned problems. The invention provides a simple and efficient process and device for obtaining highly pure aqueous cyanopyridine solutions. The quenching of cyanopyridine gas with organic solvents is not necessary. The inventive method allows the purification of the cyanopyridine, whilst maintaining hydrolysis of the cyanopyridine at a low level, for example below 2% or below 1%. Without being bound to theory, it is believed that the decrease of hydrolysis is achieved by depleting the solution of ammonia, which otherwise would increase hydrolysis in the stripping step, and by keeping the residence time of the cyanopyridine in the process low, because it does not circulate. Therefore, hydrolysis can be largely prevented, although the absorption and stripping in the column are carried out at relatively high temperatures. In contrast to the process of CN 101045706 in which the aqueous solution comprising cyanopyridine circulates, it is not necessary to keep the overall temperature and the product concentration in the aqueous solution low.

Since the concentration of the aqueous cyanopyridine solution, which is finally obtained from the column, is high, the separation of cyanopyridine from this aqueous solution, for example by means of extraction, can be carried out in a simple manner and with a low energy input. The amount of extraction solvent can be reduced.

Since the aqueous liquid in the process and device circulates, the amount of waste water produced in the process is low. Similarly, the amount of waste gas produced is low, since a large portion of the waste gas is refed into the reactor.

Even further, the yield of cyanopyridine from alkylpyridines is high, because unreacted alkylpyridines and ammonia are reintroduced into the reactor after passing the condenser.

BRIEF DESCRIPTION OF THE DRAWING

FIG. 1 shows a preferred inventive device. The components are only exemplified, and may be omitted or replaced by alternative components within the scope of the claims.

The device shown in FIG. 1 comprises a reactor (1), in which a gaseous product comprising the cyanopyridine is obtained and directed to a column (2). The gaseous product is transferred to a column (2) through a connection (10). Optionally, the gaseous product is cooled in a cooler (26). The gaseous product is introduced into the column (2) approximately in the middle and between the upper absorber section (3) and the lower stripping section (4). At the bottom of the column, there may be a boiler (5), which introduces hot steam near the bottom of the column. At the bottom of the column, there is an outlet and a connection (11) for eluting the aqueous solution comprising cyanopyridine. The solution may pass a cooler (6) and can be isolated for further use through connection (14). At the top of the column (2), there is an outlet and a connection (15) for letting out a gaseous phase depleted of cyanopyridine, which passed the absorber section (3).

The gaseous phase is passed to a condenser (7) through connection (15). The condenser (7) is adjusted to condensing the non-volatile components, i.e. the water and cyanopyridine. The volatile components are retransferred into the reactor (1) by connections (17) and (20). The gaseous phase is recycled by means of a compressor or ventilator (8). A portion of the waste gas can be discarded through connection (18) and be replaced by fresh air through connection (19). Connections (18) and (19) can be positioned anywhere in the gas cycle. The condensed aqueous phase from the condenser (7) is retransferred to the top of column (2) through connection (16). If necessary, a pump supports connection (16). The aqueous condensate is reintroduced at the top, or near the top of the column (2), such that the aqueous phase functions as an absorber liquid in the absorber section. The amount of water, which is eluted together with the cyanopyridine solution, is replaced with fresh water. It can be added anywhere in the process, for instance through a connection (21).

WORKING EXAMPLE

The inventive process was carried out in an industrial device with the components shown in FIG. 1. In the reactor, cyanopyridine was produced from methylpyridine in an ammoxidation reaction. The components, temperatures, mass flow and pressure in the device were adjusted as shown in table 1 for each compartment. The headline of the table denotes the number of each connection as shown in FIG. 1 and as explained in the corresponding description above. For example, stream No. 14 is the final product stream. As a result, a 29.7% (w/w) aqueous solution of cyanopyridine is obtained, which comprises only very low amounts of side products. The example shows that the inventive process and device allow the production of a highly pure aqueous solution of cyanopyridine.

TABLE 1

Product streams and conditions according to the working example

| | | Stream No. | | | | | | | | | | |
|---|---|---|---|---|---|---|---|---|---|---|---|---|
| | | 10 | 11 | 13 | 14 | 15 | 16 | 17 | 18 | 19 | 20 | 21 |
| Mass flow | kg/h | 19.630 | 4.229 | 1.010 | 3.219 | 22.506 | 6.095 | 18.110 | 2.935 | 3.338 | 18.513 | 1.699 |
| Temperature | °C. | 350 | 104 | 104 | 40 | 70 | 35 | 35 | 86 | 20 | 160 | 20 |
| Pressure | bar | 1.14 | 1.15 | 1.15 | 1.15 | 1.11 | | 1.10 | 1.00 | | 1.70 | |
| Components: | | | | | | | | | | | | |
| Flow rates | kg/h | 19.630 | 4.230 | 1.010 | 3.220 | 22.505 | 6.094 | 18.110 | 2.936 | 3.337 | 18.513 | 1.699 |
| Oxygen | kg/h | 400 | — | — | — | 400 | — | 400 | 65 | 678 | 1.014 | |

TABLE 1-continued

Product streams and conditions according to the working example

| | | Stream No. | | | | | | | | | | |
|---|---|---|---|---|---|---|---|---|---|---|---|---|
| | | 10 | 11 | 13 | 14 | 15 | 16 | 17 | 18 | 19 | 20 | 21 |
| Ammonia | kg/h | 92 | traces | traces | traces | 295 | 203 | 92 | 15 | — | 77 | |
| Water | kg/h | 1.170 | 3.192 | 940 | 2.252 | 4.410 | 5.492 | 617 | 100 | 107 | 625 | 1.699 |
| Methylpyridine | kg/h | 19 | traces | traces | traces | 64 | 44 | 19 | 3 | — | 16 | |
| Cyanopyridine | kg/h | 968 | 1.024 | 70 | 954 | 62 | 55 | 2 | traces | — | 1 | |
| Nitrogen | kg/h | 15.750 | — | — | — | 15.750 | — | 15.750 | 2.553 | 2.552 | 15.750 | |
| Carbon dioxide | kg/h | 1.096 | traces | traces | traces | 1.375 | 279 | 1.096 | 178 | — | 918 | |
| Hydrogen cyanide | kg/h | 135 | traces | traces | traces | 149 | 15 | 134 | 22 | — | 112 | |
| Pyridine | kg/h | traces | traces | traces | traces | traces | traces | traces | traces | — | traces | |
| Nicotinic acid | kg/h | traces | 7 | — | 7 | — | 3 | — | — | — | — | |
| Nicotinic acid amide | kg/h | traces | 7 | — | 7 | — | 3 | — | — | — | — | |

The invention claimed is:

1. A method for the production of a cyanopyridine, comprising the steps of
   (a) feeding a gaseous reaction product comprising cyanopyridine into a column (2), comprising an absorber section (3) and a stripping section (4), the absorber section being positioned above the stripping section, such that liquid which passes the absorber section (3) by gravity enters the stripping section (4),
   (b) contacting the gaseous reaction product with an aqueous phase in the absorber section (3), such that at least a portion of the cyanopyridine is dissolved in the aqueous phase to provide an aqueous solution comprising cyanopyridine,
   (c) stripping the aqueous solution obtained from the absorber section (3) in: step (b) with a stripping gas in the stripping section (4), and
   (d) eluting the aqueous solution comprising the cyanopyridine resulting from step (d)from the bottom of the column (2).

2. The method of claim 1, wherein the temperature in the absorber section (3) is between 40 to 90° C.

3. The method of claim 1, wherein the stripping gas is water steam.

4. The method of claim 1, wherein the temperature in the stripping section (4) is between 90 and 115° C.

5. The method of claim 1, wherein the aqueous solution is cooled to a temperature below 50° C. during and/or after the elution (d) by a cooler (6).

6. The method of claim 1, wherein the gaseous phase comprising the cyanopyridine is produced in a reactor (1), in which an oxidative ammonolysis of an alkylpyridine is carried out.

7. The method of claim 6, wherein the alkylpyridine is 3-methylpyridine and the cyanopyridine is 3-cyanopyridine.

8. The method of claim 1, wherein the gaseous phase, which passed the absorber section (3), is let out at the top of the column (2) and transferred to a condenser (7), in which an aqueous condensate is obtained.

9. The method of claim 8, wherein the aqueous condensate is fed into the absorber section of the column (2) and/or wherein at least a portion of the gaseous phase, which passed the condenser (7), is fed into the reactor (1).

10. The method of claim 1, wherein the process is a closed process, in which the aqueous phase, which is not eluted from the column (2) in step (d), is refluxed, and/or in which at least a portion of the gaseous phase, preferably more than 50% by volume, is refluxed.

11. A device for the production of a cyanopyridine, comprising
   a column (2) comprising an absorber section (3) and a stripping section (4),
   the absorber section (3) being positioned above the stripping section (4), such that liquid which passed the absorber section (3) enters the stripping section (4),
   means (10) for feeding a gaseous phase comprising the cyanopyridine into the column (2),
   the absorber section (3) being adapted for contacting the gaseous phase with an aqueous solution, such that at least a portion of the cyanopyridine is dissolved in the aqueous solution,
   the stripping section (4) being adapted for stripping the aqueous solution obtained from the absorber section (3) with a stripping gas, and
   means (11) at the bottom of the column (2) for eluting an aqueous solution comprising the cyanopyridine.

12. The device of claim 11, wherein the column (2) further comprises an outlet at the top and means (15) at the top of the column (2) for transferring the gaseous phase, which passed the absorber section (3), to a condenser (7), in which an aqueous condensate is obtained.

13. The device of claim 11, wherein the condenser (7) comprises means (16) for feeding the aqueous condensate from the condenser (7) into the absorber section (3) of the column (2) and/or means (17, 20) for transferring the gaseous phase, which passed the condenser (7), into the reactor (1).

14. The device of claim 11, further comprising a boiler for providing water steam to the stripping section (4) and/or a cooler (6) for cooling the aqueous solution after the elution (e).

15. The device of claim 11, comprising a cyanopyridine.

* * * * *